(12) United States Patent
Eshoo et al.

(10) Patent No.: US 9,279,145 B2
(45) Date of Patent: Mar. 8, 2016

(54) BUFFERS FOR THE STABLE STORAGE OF NUCLEIC ACIDS

(75) Inventors: Mark W. Eshoo, Solana Beach, CA (US); David D. Duncan, Encinitas, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 161 days.

(21) Appl. No.: 13/340,976

(22) Filed: Dec. 30, 2011

(65) Prior Publication Data

US 2012/0171685 A1    Jul. 5, 2012

Related U.S. Application Data

(60) Provisional application No. 61/428,635, filed on Dec. 30, 2010.

(51) Int. Cl.
*C07H 21/02* (2006.01)
*B01J 19/00* (2006.01)
*C12Q 1/68* (2006.01)

(52) U.S. Cl.
CPC .................................... *C12Q 1/6806* (2013.01)

(58) Field of Classification Search
CPC ..................................................... C12Q 1/6806
USPC ............................. 536/23.1; 422/41; 435/6.1
See application file for complete search history.

(56) References Cited

U.S. PATENT DOCUMENTS

| 5,858,988 | A  | 1/1999 | Wang |
| 6,258,320 | B1 | 7/2001 | Persing et al. |
| 6,673,621 | B1 | 1/2004 | Mitchell |
| 2009/0216213 | A1 | 8/2009 | Muir et al. |
| 2009/0233309 | A1* | 9/2009 | Fischer et al. ..................... 435/6 |
| 2010/0173392 | A1 | 7/2010 | Davis et al. |

OTHER PUBLICATIONS

Sigma-Aldrich. Corning Costar Spin-X centrifuge tube filters; www.sigmaaldrich.com/catalog/product/sigma/cls8162?lang=eng&region=US; retrieved Jun. 24, 2013.*
Thorne et al. In vitro amplification of PrPSc derived from the brain and blood of sheep infected with scrapie. J General Virology 2008;89:3177-84.*
Tsuchiya et al. The "spanning protocol": a new DNA extraction method for efficient single-cell genetic diagnosis; J Assisted Repro and Genet 2005;22(11/12):407-14.*
Subramanian et al. Triplet repeats in human genome: distribution and their association with genes and other genomic regions. Boinformatics 2003;19(5):549-52.*
Green H., et al., "Codon Reiteration and the Evolution of Proteins," Proceedings of the National Academy of Sciences, 1994, vol. 91 (10), pp. 4298-4302.
International Search Report and Written Opinion for Application No. PCT/US2011/068052, mailed on May 2, 2012, 10 pages.

* cited by examiner

*Primary Examiner* — Jezia Riley
(74) *Attorney, Agent, or Firm* — David A. Casimir; Casimir Jones, S.C.

(57) ABSTRACT

Provided herein are buffers for the stabilization of nucleic acid molecules. The buffers find particular use for the stabilization of trace amounts of nucleic acid molecules in a variety of environments, including repeated freeze/thaw cycles. For example, in some embodiments, provided herein are compositions comprising tris(hydroxymethyl)aminomethane (Tris), ethylenediaminetetraacetic acid (EDTA), polyadenylic acid, and a synthetic DNA oligonucleotide.

19 Claims, 2 Drawing Sheets

SEQUENCE LISTING

```
<160> NUMBER OF SEQ ID NOS: 6

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aataataata ataataataa taataataat aataataata ataataataa taataataat      60
aataat                                                                  66

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaaaaaaa                                                              10

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaaaaaaaa aaaaaaaaaa aaaaa                                             25

<210> SEQ ID NO 4
<211> LENGTH: 50
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 4
aaaaaaaaaa aaaaaaaaaa aaaaaaaaaa aaaaaaaaaa aaaaaaaaaa                    50

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aaaaaaaaaa aaaaaaaaaa aaaaaaaaaa aaaaaaaaaa aaaaaaaaaa aaaaaaaaaa         60
aaaaaaaaaa aaaaaaaaaa aaaaaaaaaa aaaaaaaaaa                              100

<210> SEQ ID NO 6
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
aaaaaaaaaa aaaaaaaaaa aaaaaaaaaa aaaaaaaaaa aaaaaaaaaa aaaaaaaaaa         60
aaaaaaaaaa aaaaaaaaaa aaaaaaaaaa aaaaaaaaaa aaaaaaaaaa aaaaaaaaaa        120
aaaaaaaaaa aaaaaaaaaa aaaaaaaaaa aaaaaaaaaa aaaaaaaaaa aaaaaaaaaa        180
aaaaaaaaaa aaaaaaaaaa                                                    200
```

BUFFERS FOR THE STABLE STORAGE OF NUCLEIC ACIDS

The present Application claims priority to U.S. Provisional Application Ser. No. 61/428,635 filed Dec. 30, 2010, the entirety of which is herein incorporated by reference.

FIELD

Provided herein are buffers for the stabilization of nucleic acid molecules. The buffers find particular use for the stabilization of trace amounts of nucleic acid molecules in a variety of environments, including repeated freeze/thaw cycles. For example, in some embodiments, provided herein are compositions comprising tris(hydroxymethyl)aminomethane (Tris), ethylenediaminetetraacetic acid (EDTA), polyadenylic acid, and a synthetic DNA oligonucleotide.

BACKGROUND

Storage and handling of nucleic acid molecules, and particularly small amounts of nucleic acid molecules, is complicated by the break-down of the nucleic acid molecules over time or in response changes in the environment (e.g., temperature changes). For research, diagnostic, and clinical applications that require minimal amounts of nucleic acid break-down, the art is in need of additional compositions and methods for stabilizing nucleic acid during storage and handling.

SUMMARY

Provided herein are buffers for the stabilization of nucleic acid molecules. The buffers find particular use for the stabilization of trace amounts of nucleic acid molecules in a variety of environments, including repeated freeze/thaw cycles. For example, in some embodiments, provided herein are compositions comprising one or more or all of tris(hydroxymethyl)aminomethane (Tris), ethylenediaminetetraacetic acid (EDTA), polyadenylic acid, and a synthetic DNA oligonucleotide.

Thus, in some embodiments, provided herein are buffers comprising, consisting of, or consisting essentially of tris (hydroxymethyl)aminomethane (Tris), ethylenediaminetetraacetic acid (EDTA), polyadenylic acid, and a synthetic DNA oligonucleotide. In some embodiments, the buffer further contains a nucleic acid of interest to be stabilized. In some embodiments, the nucleic acid of interest is present in small amounts (e.g., less than 100 ng/µl, less than 50 ng/µl, less than 20 ng/µl, less than 10 ng/µl, less than 1 ng/µl, etc.). The buffers may be provided in concentrated (e.g., 2×, 5×, 10×, 20×, 50×, etc.) or unconcentrated forms as a liquid or frozen solid. The buffers may be provided in kit form in one or more containers (e.g., bottles, bags, boxes, tubes, vials, ampules, wells, microfluidic devices, channels). Kits may further include any other components useful, necessary, or sufficient for practicing any of the methods described herein, such components including, but not limited to, positive and negative control reagents, instructions, software, enzymes, labels, instruments, solid supports (e.g., slides, beads, etc.), and the like.

Further provided herein are reaction mixtures containing the buffers and one or more other components. Such other components include, but are not limited to, enzymes (e.g., polymerases, ligases, nucleases), nucleic acid molecules (e.g., DNA, RNA, tRNA, rRNA), labels (fluorophores, radionucleotides, antibodies, dyes), linkers, ligands, and the like.

Further provided herein are methods for storing and handling nucleic acid molecules comprising: contacting a nucleic acid molecule of interest with any of the buffers described herein. In some embodiments, the nucleic acid of interest is present in small amounts. In some embodiments, the nucleic acid of interest is free of contaminating DNA or RNA, i.e. other than a nucleic acid present in the buffer provided herein (e.g., synthetic DNA oligonucleotide and polyadenylic acid). In some embodiments, the nucleic acid of interest, in the presence of the buffer, undergoes one or more (e.g., 2, 3, 4, 5, 6, 7, 8, 9, 10, ... ) freeze/thaw events. In some embodiments, the nucleic acid of interest is a reference DNA sample that is employed as a standard for quantitative analysis of other nucleic acid molecules (e.g., in quantitative PCR reactions, nucleic acid dilution experiments, mass spectrometry, etc.) or as a calibrant. In some embodiments, the nucleic acid of interest is a trace DNA or RNA specimen whose condition and/or amount is important to maintain, such as, for example, nucleic acid from forensic samples, diagnostic samples (e.g., single cells), ancient samples, and the like.

In some preferred embodiments, the buffer is: 1) free of any agent that will create an undesired signature or background signal in an assay format in which the buffer is employed (e.g., mass spectroscopy, fluorescence detection, luminescence detection, phosphorescence detection, colorimetric detection, ELISA, etc.); 2) free of nucleases; and 3) free of any agent that will interfere with assay performance (e.g., salts or other components that inhibit or otherwise adversely impact enzyme activity in reactions such as PCR reactions and next generation sequencing reactions or that hinder mass spectrometric or other analyses).

In some embodiments, the nucleic acid of interest is a single-stranded nucleic acid, a double-stranded nucleic acid, a plasmid, an siRNA, a hairpin nucleic acid, a fosmid, a cosmid, a BAC, an oligonucleotide, a polynucleotide, genomic DNA, metagenomic DNA, or an amplicon.

Accordingly, herein are provided compositions, methods, and uses related to storing trace amounts of nucleic acids. In some embodiments, the composition comprises a dilution buffer. In some embodiments, the dilution buffer further comprises a synthetic oligonucleotide and in some embodiments the dilution buffer further comprises polyadenylic acid. Embodiments of the technology herein provide a composition for storing nucleic acids comprising a pH buffer, a chelator, a polyadenylic acid, and a synthetic oligonucleotide. While not limited in the buffer that is used, some embodiments provide that the pH buffer is Tris. Also, while not limited in the chelator that is used, in some embodiments the chelator is EDTA. Some embodiments provide that the synthetic oligonucleotide is poly-AAT; in some specific embodiments, the synthetic oligonucleotide is $(AAT)_{22}$ (SEQ ID NO:1). In some embodiments, the pH of the pH buffer is approximately 8.0.

Embodiments of the technology provided herein comprise a composition in which the concentration of the pH buffer is 10 mM, the concentration of the chelator is 50 µM, the concentration of the polyadenylic acid is 20 µg/ml, and the concentration of the synthetic oligonucleotide is 20 µg/ml. In some embodiments, the pH buffer is 10 mM Tris (pH 8.0), the chelator is 50 µM EDTA, and the synthetic oligonucleotide is 20 µg/ml poly-AAT. In some embodiments, the synthetic oligonucleotide is $(AAT)_{22}$ (SEQ ID NO:1). Other embodiments employ different concentrations of one or more components (e.g., greater or less than the above concentrations by 10%, 20%, 50%, 100%, 200%, etc.).

Some embodiments provide a composition comprising DNA/RNA-free water, 0.0001 ml of 0.5 M EDTA, 0.01 ml of 1 M Tris (pH 8.0), 2 pl of 10 mg/ml polyadenylic acid, and 2 µl of 10 mg/ml synthetic oligonucleotide. In some embodiments, the composition is packaged in a sterile screw-top tube. In some embodiments the composition does not comprise a nuclease, a microbe, or nucleic acid other than the polyadenylic acid and the synthetic oligonucleotide.

Also provided herein are methods related to storing nucleic acids. Embodiments of said methods provided comprise providing a sterile storage vessel of an appropriate size to contain a volume of storage solution required and mixing a pH buffer, a chelator, a polyadenylic acid, and a synthetic oligonucleotide in water to provide the volume of storage solution required. Some embodiments provide a method comprising providing a sterile storage vessel of an appropriate size to contain a volume of storage solution required; adding to the sterile storage vessel a first volume of water that is approximately 60% of the volume of storage solution required; adding to the sterile storage vessel a volume of 0.0001 ml of 0.5 M EDTA per 1 ml of the volume of storage solution required; adding to the sterile storage vessel a volume of 0.010 ml of 1 M Tris (pH 8.0) per 1 ml of the volume of storage solution required; adding to the sterile storage vessel a volume of 2 µl of 10 mg/ml polyadenylic acid per 1 ml of the volume of storage solution required; adding to the sterile storage vessel a volume of 2 µl of 10 mg/ml poly-AAT per 1 ml of the volume of storage solution required; adding a second volume of water required to bring the total volume of the storage solution to the volume of storage solution required; and mixing the storage solution to homogeneity. In some embodiments, amounts are added on a per-gram basis rather than on a per-milliliter basis. In some embodiments, the method further comprises storing the storage solution at −20 C and in some embodiments the method further comprises preparing a nucleic acid solution in an appropriate volume of the storage solution; freezing the nucleic acid solution; and thawing the nucleic acid solution. In some embodiments, the sterile storage vessel is polypropylene. In some embodiments, the water is free of DNA, RNA, nucleases, and microbes.

Some embodiments provide a method comprising performing a mass spectrometry analysis on a nucleic acid solution in an appropriate volume of the storage solution.

Additional embodiments relate to uses of the compositions provided herein. For example, embodiments provide for use of the composition of claim 1 for the stable storage of nucleic acid. In some embodiments, the concentration of the stored nucleic acid is less than 20 ng/µl. In some embodiments, the composition is used to prepare a standard or calibrant. Some embodiments provide for use of a nucleic acid in a storage solution for mass spectrometry.

DESCRIPTION OF THE DRAWINGS

These and other features, aspects, and advantages of the present technology will become better understood with regard to the following drawings.

DETAILED DESCRIPTION

Figure 1:
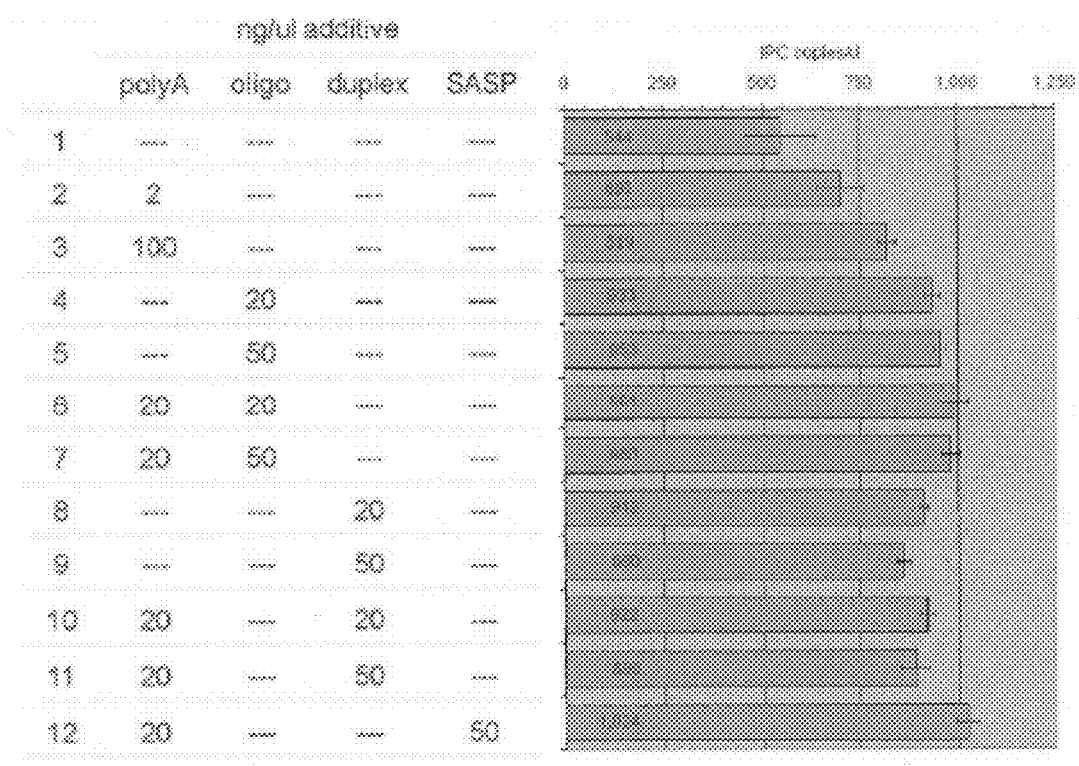
FIG. 1 is a plot showing the recovery of DNA from nucleic acid storage buffers comprising polyadenylic acid (polyA), a single-stranded synthetic oligonucleotide (oligo), a duplex oligonucleotide (duplex), and salmon sperm DNA (SASP).

Provided herein are buffers for the stabilization of nucleic acid molecules. The buffers find particular use for the stabilization of trace amounts of nucleic acid molecules in a variety of environments, including repeated freeze/thaw cycles. For example, in some embodiments, provided herein are compositions comprising tris(hydroxymethyl)aminomethane (Tris), ethylenediaminetetraacetic acid (EDTA), polyadenylic acid, and a synthetic DNA oligonucleotide.

Definitions

To facilitate an understanding of the present technology, a number of terms and phrases are defined below. Additional definitions are set forth throughout the detailed description.

As used herein, "a" or "an" or "the" can mean one or more than one. For example, "a" cell can mean one cell or a plurality of cells.

As used herein, the term "oligonucleotide" refers to a short polynucleotide, typically less than or equal to 150 nucleotides long (e.g., in the range of 5 and 150, preferably in the range of 10 to 100, more preferably in the range of 15 to 50 nucleotides in length). However, as used herein, the term is also intended to encompass longer or shorter polynucleotide chains.

As used herein, a "polynucleotide" refers to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The term "polynucleotide" includes, without limitation, single- and double-stranded polynucleotide. The term "polynucleotide" as it is employed herein embraces chemically, enzymatically or metabolically modified forms of polynucleotide. "Polynucleotide" also embraces a short polynucleotide, often referred to as an oligonucleotide (e.g., a primer or a probe). A polynucleotide has a "5'-terminus" and a "3'-terminus" because polynucleotide phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a polynucleotide sequence, even if internal to a larger polynucleotide (e.g., a sequence region within a polynucleotide), also can be said to have 5'- and 3'ends.

Embodiments of the Technology

Although the disclosure herein refers to certain illustrated embodiments, it is to be understood that these embodiments are presented by way of example and not by way of limitation.

Herein provided are compositions for storing nucleic acids, methods of preparing compositions for storing nucleic acids, and methods of using compositions for storing nucleic acids. In some embodiments, the composition comprises a pH buffer, a chelator, a polyadenylic acid, and a synthetic oligonucleotide.

1. pH Buffers

Some embodiments of the technology provided herein comprise a pH buffer. In general, a buffer is an aqueous solution consisting of a mixture of a weak acid and its conjugate base or a weak base and its conjugate acid. Buffered solutions have the property that the pH of the solution changes very little when a small amount of strong acid or base is added to it. Accordingly, buffer solutions are used to maintain pH at a nearly constant value in a wide variety of chemical applications. Nucleic acids are susceptible to degradation at extreme pH, i.e., in very acidic or in very basis solutions. Thus, buffers prevent or minimize the degradation of a nucleic acid in solution.

Many types of substances are used as a pH buffer provided that the pH of the solution changes very little when a small amount of strong acid or base is added to it. For example, TAPS (3-((tris(hydroxymethyl)methyl)amino) propanesulfonic acid, Bicine (N,N-bis(2-hydroxyethyl)) glycine, Tris (tris(hydroxymethyl) methylamine), Tricine (N-tris(hydroxymethyl) methylglycine), HEPES (4-2-hydroxyethyl-1-piperazine ethanesulfonic acid), TES (2-((tris(hydroxymethyl) methyl)amino) ethanesulfonic acid), MOPS (3-(N-morpholino) propanesulfonic acid), PIPES (piperazine-N,N'-bis(2-ethanesulfonic acid)), Cacodylate (dimethylarsinic acid), SSC (saline sodium citrate), and MES (2-(N-morpholino)ethanesulfonic acid) are pH buffers (e.g., for biological samples (e.g., nucleic acids)). The following pairs of compounds are also used to make buffers: HCl/sodium citrate; citric acid/sodium citrate, acetic acid/sodium acetate, $K_2HPO_4/KH_2PO_4$, $Na_2HPO_4/NaH_2PO_4$, and borax/sodium hydroxide. In some embodiments provided herein, the pH buffer is Tris. In some embodiments, the pH is maintained at approximately 8.0.

2. Chelators

Some embodiments of the technology provided herein comprise a chelator. Chelators are polydentate molecules that form multiple interactions with a metal ion. In general, a chelator is a substance that forms a soluble, complex molecule with certain metal ions, inactivating the ions so that they cannot participate or interact normally with other elements, ions, or molecules. Many enzymes (i.e., metalloenzymes, e.g., some nucleases) require a metal ion for activity. A chelator can thus be used to sequester the metal ions and prevent them from interacting with enzyme polypeptides and thus eliminating, inhibiting, or minimizing the enzyme activity. In addition, some metal ions in and of themselves can attack and degrade biological molecules (e.g., nucleic acid). Accordingly, a chelating agent maintains the integrity of a nucleic acid in solution.

For example, EDTA (Ethylene diamine tetraacetic acid), EGTA (ethylene glycol tetraacetic acid), and BAPTA (1,2-bis(o-aminophenoxy)ethane-N,N,N',N'-tetraacetic acid), DTPA isothiocyanate ((S)-1-p-isothiocyanato benzyldiethylene triaminepentaacetic acid), and TPEN (tetrakis-(2-pyridylmethyl) ethylenediamine) are chelators appropriate for solutions intended for storage of biological molecules (e.g., nucleic acid). Some embodiments of the technology provided herein comprise the chelator EDTA.

3. Synthetic Oligonucleotides

Some embodiments of the technology provided herein comprise a synthetic oligonucleotide. An oligonucleotide is a short nucleic acid polymer (e.g., typically having fewer than 200, fewer than 100, or fewer than 50 bases). Typically, oligonucleotides are chemically synthesized using protected phosphoramidite derivatives of nucleosides or nucleoside analogs. Highly purified synthetic oligonucleotides are readily available from numerous commercial suppliers (e.g., DNA Technologies, Operon, Invitrogen, and Integrated DNA Technologies). As used herein, oligonucleotide can refer to a polynucleotide, an oligodeoxyribonucleotide, a primer, an oligoribonucleotide, a peptide nucleic acid, a phosphorothioate oligonucleotide, and the like. Some embodiments of the technology provided herein comprise an oligonucleotide. In some embodiments, the sequence of bases in the oligonucleotide comprises repeats of a shorter sequence, e.g., repeats of the sequence AAT (i.e., deoxyadenosine-deoxyadenosine-deoxythymidine . . . ) to form the base sequence of the synthetic oligonucleotide (i.e., poly-AAT). In some embodiments the sequence AAT is repeated 22 times (i.e., $(AAT)_{22}$) to form the sequence of the oligonucleotide (i.e., 5'-AATAATAATAATAATAATAATAATAATAATAATAATAATAATAATAATAATAATAATAATAATAAT-3')(SEQ ID NO:1).

4. Polyadenylic Acid

Some embodiments of the technology provided herein comprise polyadenylic acid. Polyadenylic acid is an oligonucleotide (e.g., an oligoribonucleotide or polyribonucleotide) consisting essentially of one or more adenine bases (e.g., $A_5$, $A_{10}$ (SEQ ID NO:2), $A_{25}$ (SEQ ID NO:3), $A_{50}$ (SEQ ID NO:4), $A_{100}$ (SEQ ID NO:5), $A_{200}$ (SEQ ID NO:6), etc.) and is also known as poly-A or poly-rA. Polyadenylic acid can be synthesized or isolated from a natural source. Polyadenylic acid is readily available from numerous commercial suppliers.

EXAMPLES

Example 1

Experiments were conducted during the development of embodiments of the technology to identify which, if any, of numerous possible buffer components would provide a desired effect. The pUC199 plasmid was used as a test DNA to evaluate potential buffer compositions. Plasmid DNA was quantified using quantitative PCR (Taqman).

In a first set of experiments, twenty-one formulations were employed to determine their effect, if any, on the number of copies of pUC199 plasmid present after three freeze-thaw cycles and amplification. Of these tested materials, polyA nucleic acid (20 ng/µl) and salmon sperm DNA (SASP) (20 ng/µl) provided the highest recoveries (1,175 and 1,357 copies of plasmid per µl of sample, respectively, compared to 381 for a water control). A dA:dT oligonucleotide (2 ng/µl) provided 986 copies/µl. In view of these findings, a combination of both polyA and SASP was tested and compared to individual treatments resulting in 912 copies/µl for the polyA (20 ng/µl), 967 for the SASP (50 ng/µl), and 1008 for the combination (20 ng/µl, 50 ng/µl) relative to 266 for the water control. Further experiments were conducted to test the combination of polyA/SASP. An amount of 100 ng/µl of polyA alone was compared to a treatment with 20 ng/µl polyA:50 ng/µl SASP. The recovery was 10% higher for the polyA/SASP combination.

The polyA-SASP buffer was tested with a nucleic acid detection product and platform, specifically, a PCR/mass spectroscopy-based detection system for identifying the presence of bacterial sequences in a sample (see Ecker et al. (2006) "The Ibis T5000 Universal Biosensor: An Automated Platform for Pathogen Identification and Strain Typing" JALA 6(11)341-351). The buffer resulted in undesired DNA signatures, which may be a result of SASP being a natural product, although an understanding of the mechanism is not needed, nor is the present invention limited to any particular mechanism of action.

In view of these findings, additional buffer compositions were tested. In one set of experiments, synthetic DNA with and without polyA was tested. In particular, a 66-nucleotide synthetic DNA (i.e., $(AAT)_{22}$ (SEQ ID NO:1)) was used, as well as the reverse complement. Both single-stranded and duplex versions were tested. Three tests were employed: functional plasmid recovery after 3 thaw-freeze cycles, a bacterial detection assay using the PCR/mass spectroscopy technique, and an extended RNase/DNase test (4-day testing of 20 µl test nucleic acid in buffer to determine any long-term break-down, e.g., by a nuclease). The results of the plasmid recovery assay are shown in FIG. 1. These results show a positive impact of the synthetic oligonucleotide alone, both in single-stranded and duplex forms, and an even better impact with the combination of the synthetic oligonucleotide and the polyA. Each of the synthetic DNA samples passed the nuclease test, demonstrating that no relevant nuclease activity had occurred after four days. Likewise, the synthetic DNA-containing buffers did not produce any undesired signatures in the PCR/mass spectroscopy test.

Figure 2:
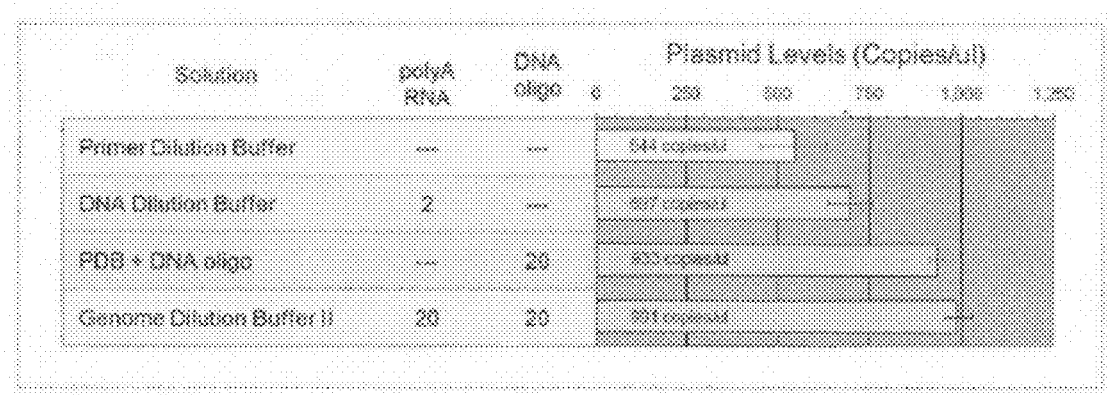
FIG. 2 is a plot showing recovery of DNA from nucleic acid storage buffers comprising polyadenylic acid (polyA RNA) and an oligonucleotide.

Tests were conducted to compare the recovery of low levels of plasmid formulated in various buffers: 1) "primer dilution buffer" (EDTA/Tris); 2) "DNA dilution buffer" (EDTA/Tris/polyA); 3) "PDB+DNA oligo (EDTA/Tris/synthetic oligo); and 4) "Genome Dilution Buffer II" (EDTA/Tris/polyA/synthetic oligo). Data represent 8 replicate experiments conducted in 2-ml Sarstedt tubes with three thaw/freeze cycles and copies determined by QPCR. The results are shown in FIG. 2, which demonstrated that the combination of the polyA and synthetic oligonucleotide provided the best result.

Example 2

This example provides an illustrative commercial formulation of one embodiment of the technology. A kit is provided containing a buffer with that in useable form is (per mL): 0.9859 g DNA/RNA free water; 0.0001 mL 0.5M EDTA (Q-100 processed); 0.010 mL 1M Tris pH 8.0 (Q-100 processed); 2 µl polyadenylic acid (sonicated, 10 mg/mL); and 2 µl synthetic $(AAT)_{22}$ (SEQ ID NO:1) 10 mg/mL. The kit further comprises centrifuge tubes (15 mL or 50 mL), a 2-mL Sarstedt screw-top tube, DNAse/RNase contamination testing reagents; and bacterial contamination testing reagents.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition for storing nucleic acids comprising a pH buffer, a chelator, a polyadenylic acid $(C_{10}H_{14}N_5O_7P)_n$ wherein "n" has a value from 2 to 200, a synthetic oligonucleotide, wherein the synthetic oligonucleotide is $(AAT)_{22}$ (SEQ ID NO: 1), a storage vessel, and a stored nucleic acid.

2. The composition of claim 1, wherein the pH buffer is Tris.

3. The composition of claim 1, wherein the chelator is EDTA.

4. The composition of claim 1, wherein a pH buffer has a pH of approximately 8.0.

5. The composition of claim 1, wherein the pH buffer has a concentration of 10 mM, the chelator has a concentration of 50 μM, the polyadenylic acid has a concentration of 20 μg/ml, and the synthetic oligonucleotide has a concentration of 20 μg/ml.

6. The composition of claim 1, wherein the pH buffer is 10 mM Tris (pH 8.0), the chelator is 50 μM EDTA, and the synthetic oligonucleotide is 20 μg/ml.

7. A composition comprising DNA/RNA-free water, 0.0001 ml of 0.5 M EDTA, 0.01 ml of 1 M Tris (pH 8.0), 2 μl of 10 mg/ml polyadenylic acid $(C_{10}H_{14}N_5O_7P)n$ wherein "n" has a value from 2 to 200, and 2 μl of 10 mg/ml synthetic oligonucleotide, wherein the synthetic oligonucleotide is $(AAT)_{22}$ (SEQ ID NO: 1).

8. The composition of claim 1, wherein the storage vessel is a sterile screw-top tube.

9. The composition of claim 1, wherein the composition does not comprise a nuclease, a microbe, or nucleic acid other than the polyadenylic acid and the synthetic oligonucleotide.

10. A method comprising:
a) providing a sterile storage vessel of an appropriate size to contain a volume of storage solution required; and
b) mixing a pH buffer, a chelator, a polyadenylic acid $(C_{10}H_{14}N_5O_7P)_n$ wherein "n" has a value from 2 to 200, and a synthetic oligonucleotide, wherein the synthetic oligonucleotide is $(AAT)_{22}$ (SEQ ID NO: 1), in water to provide the volume of storage solution required.

11. A method comprising:
a) providing a sterile storage vessel of an appropriate size to contain a volume of storage solution required;
b) adding to the sterile storage vessel a first volume of water that is approximately 60% of the volume of storage solution required;
c) adding to the sterile storage vessel a volume of 0.0001 ml of 0.5 M EDTA per 1 ml of the volume of storage solution required;
d) adding to the sterile storage vessel a volume of 0.010 ml of 1 M Tris (pH 8.0) per 1 ml of the volume of storage solution required;
e) adding to the sterile storage vessel a volume of 2 μl of 10 mg/ml polyadenylic acid $(C_{10}H_{14}N_5O_7P)_n$ wherein "n" has a value from 2 to 200 per 1 ml of the volume of storage solution required;
f) adding to the sterile storage vessel a volume of 2 μl of 10 mg/ml poly-AAT, wherein the poly-AAT is $(AAT)_{22}$ (SEQ ID NO: 1), per 1 ml of the volume of storage solution required;
g) adding a second volume of water required to bring the total volume of the storage solution to the volume of storage solution required; and
h) mixing the storage solution to homogeneity.

12. The method of claim 11 further comprising the step of:
i) storing the storage solution at −20 ° C.

13. The method of claim 11, further comprising the steps of:
   i) preparing a nucleic acid solution in an appropriate volume of the storage solution;
   j) freezing the nucleic acid solution; and
   k) thawing the nucleic acid solution.

14. The method of claim 10, wherein the sterile storage vessel is polypropylene.

15. The method of claim 10, wherein the water is free of DNA, RNA, nucleases, and microbes.

16. The composition of claim 1, wherein said composition is salt free.

17. The composition of claim 7, wherein said composition is salt free.

18. The method of claim 10, wherein said storage solution is salt free.

19. The method of claim 11, wherein said storage solution is salt free.

* * * * *